United States Patent [19]

Terness et al.

[11] Patent Number: 5,004,604

[45] Date of Patent: Apr. 2, 1991

[54] IMMUNO-SUPPRESSIVE MATERIAL AND PROCESS FOR PREPARING SAME

[75] Inventors: Peter Terness; Gerhard Opelz, both of Heidelberg, Fed. Rep. of Germany

[73] Assignee: Fresenius A. G., Bad Homburg, Fed. Rep. of Germany

[21] Appl. No.: 178,643

Related U.S. Application Data

[63] Continuation-in-part of PCT DE87/00339, filed Aug. 1, 1987, published as WO88/00836 on Feb. 11, 1988.

[22] Filed: Mar. 25, 1988

[30] Foreign Application Priority Data

Aug. 1, 1986 [DE] Fed. Rep. of Germany .... 3626110.6

[51] Int. Cl.[5] ...................... A61K 37/66; A61K 35/14
[52] U.S. Cl. ................................. 424/85.5; 424/85.1; 424/85.8; 530/350; 530/351; 530/364; 530/380; 530/387; 530/412
[58] Field of Search .................... 424/85.5, 85.1, 85.8; 530/351, 387, 350, 364, 380, 412

[56] References Cited

U.S. PATENT DOCUMENTS 4,728,614 3/1988 Lau ...................................... 530/351

OTHER PUBLICATIONS

Jakobsen et al., "Rabbit Anti Rat Lymphocyte Serum: Immunosuppression Mediated by a Pure IgM", Chemical Abstracts, vol. 80, p. 330, Ref. #131527b, 1974.
Jakobsen et al., Acta Pathol. Microbiol. Scand. Sect. B, 81(5), pp. 635–640, 1973.

*Primary Examiner*—Margaret Moskowitz
*Assistant Examiner*—Abdel A. Mohamed
*Attorney, Agent, or Firm*—Behr, Omri M.

[57] ABSTRACT

An immuno-suppressor is described in the form of an immuno-suppressor serum and/or an IS-IgG extracted from this serum, produced by immunisation of an animal with antibody-covered cells; also described is the process for making said immuno-suppressor and its use for suppressing the humoral and/or cellular immune response.

6 Claims, 5 Drawing Sheets

Fig. 3 primary antibody response

Fig. 4 secondary antibody response

IMMUNO-SUPPRESSIVE MATERIAL AND PROCESS FOR PREPARING SAME

This application is a continuation-in-part of PCT application, PCT/DE87/00339, filed 1 August, 1987 which in turn claims priority of Federal German Application P 36 26 110.6, filed 1 August, 1986.

FIELD OF THE INVENTION

The present invention is directed to an immuno-suppressive material and process for the production thereof, as well as methods of use thereof.

STATE OF THE ART

Immuno-suppressive techniques occupy an important position in human medicine. The most important indications for this therapy are: organ transplants, immune-hematological syndrome, immuno-pathologically caused diseases of the liver and collagen diseases.

The immuno-suppressives utilized heretofore in clinical work, have a substantial number of side effects, partly as a result of toxicological properties of the materials, partly as the result of a broad immuno-suppressive action.

Thus, Cyclosporin which is utilized in organ transplants, while showing exceedingly powerful immuno-suppressive action, possesses a number of toxic side effects, for example, nephro-toxicity and hepato-toxicity, which give rise to problems in clinical use. An important role in the treatment of rejection crisis after organ transplants, has been played by anti-lymphocyte globulin (ALG). Unfortunately, the production of such product having assured immuno-suppressive action and minimal toxicity, still remains problematical.

Next, encouraging results were shown by the action of selectively acting monoclonal antibodies (for example, OKT 3, T 12, anti-lymphoblast antibodies). Also here, further studies have failed to fulfill the desired goals completely.

SUMMARY OF THE INVENTION

The goal of the present invention is therefore to provide an immuno-suppressive material which has a powerful suppressive action solely upon a predetermined antigen (antigen-specific) is neither toxic nor cytotoxic and induces long acting immuno-suppression after treatment for a predetermined but limited length of time.

In accordance with the present invention this problem was solved by an immuno-suppressive material obtained by the immunization of animals with cells coated with antibodies.

This immuno-suppressive material, as provided in accordance with the present invention, comprises an immuno-suppressive serum and/or an immuno-suppressive IgG.

Among the cells suitable for this purpose there may be mentioned blood cells, spleen cells, bone marrow cells and the like, among which blood cells are particularly preferred.

The antibodies may be provided in the form of monopolyclonal antibodies or antisera, preferably polyclonal antibodies are utilized.

The recovery or production of the immuno-suppressive material in accordance with the procedure of the present invention, occurs in that cells taken from an animal are incubated with homologous or heterologous antibodies, these cells are injected into an animal, after an incubation period, blood is extracted from the injected animal and, in ways known to the art, the serum (that is to say, immuno-suppressive serum, hereinafter IS-serum), is isolated and also IgG, that is to say, immuno-suppressive IgG, hereinafter IS-IgG, is separated in a manner also known to the art.

In the separation of the IS-serum from the blood, the blood is permitted to coagulate for from about 3 to about 24 hours, suitably at room temperature. The material is then subjected to centrifugation, suitably for about 10 minutes at about 4,000 rpm, whereby the serum is separated as the supernate and can be removed. The IS-serum is then subjected to ion exchange chromatography, suitably on a Mono-Q or Q-Sepharose Fast Flow column (Trademarked product sold by Pharmacia Fine Chemicals, AB, Uppsala, Sweden), in accordance with the general procedure set forth in Separation News, 1982/1, published by Pharmacia Fine Chemicals, which is incorporated herein by reference and made part hereof. Elution with phosphate buffer (suitably 0.3M, pH 6.5) yields 3 peaks of which the first is the IgG peak. Yet a further purification step may be carried out utilizing a Protein A gel, suitably Affi-Gel Protein A Agarose (manufactured by Biorad) in accordance with the procedures set forth in the Affi-Gel Protein A MAPS II Instruction Kit Manual, published by Biorad, the disclosure of which is incorporated by reference and made part hereof.

In this procedure the IgG solution is placed upon the column in the provided binding buffer and eluted with the provided elution buffer. The eluate is rebuffered on Sephadex G25. The product may, if desired, be further purifed to provide anti-human IgG antibodies by affinity chromatography utilizing Sepharose coated with human IgG in accordance with the procedures set forth in Affinity Chromatography Principals and Methods, published by Pharmacia Fine Chemicals, 1983/2, which is incorporated herein by reference and made a part hereof.

The injection or processing of the cells taken from the animal, (i.e., blood, blood cells and the like), with homologous or heterologous antibodies, is carried out according to the procedures of the present invention, in methods and conditions well known in the art. For example, the incubation time is from about 30 to about 60 minutes and the incubation is suitably carried out at 4° C., room temperature, (that is to say, 22° C.) or even at 37° C., preferably at room temperature.

The cells covered with antibody obtained as a result of such incubation, are thereafter injected into an animal. In accordance with the preferred embodiment of the process of the present invention, the cells coated with antibodies after incubation are washed prior to injection into the animal Suitable media for this washing are cell culture media, such as the conventional phosphate buffer solution, RPMI, Hanks, and the like.

The injection of the cells coated with antibody into the animal is carried out in accordance with conventional immunization methods and under conventional immunization conditions. Suitably, the injection may take place several times, suitably 3 times. It is preferred to utilize an incubation time of from about 3 to 24 days, wherein the animals are maintained at room temperature.

The cells taken from one animal and coated with antibodies can, in accordance with the present invention, be reinjected into the same animal or, alternatively, they can be injected into another, that is to say, an animal different from the donor animal, wherein in the latter case, the animal may belong to either the same or a different species. Examples of animals suitable in the present invention may be mentioned: rats, mice, rabbits, and the like.

Figure 1:
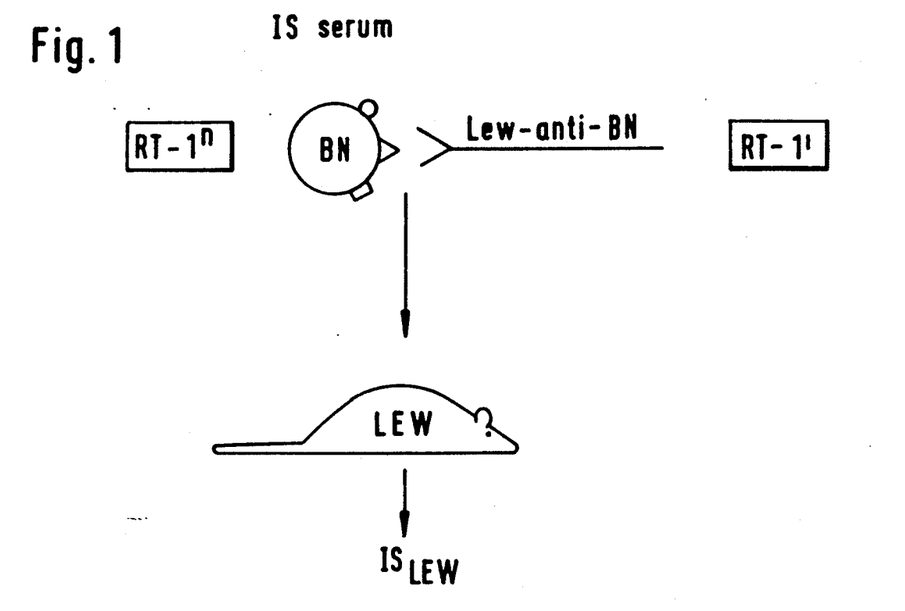
FIG. 1 is a schematic illustration of the formation of rat immune serum from LEW rats.

For example, in accordance with the present invention, rat IS-serum was produced in the highly incompatible BN→LEW system (as schematically illustrated in FIG. 1), as well as in other systems and similarly utilized.

Further, rabbit IS-serum can be obtained by the immunization of rabbits with autologous or allogeneic blood cells covered with antibodies.

A serum produced by use of antigen-bound autologous or heterologous antibodies demonstrates strong suppressive action without containing cytotoxic antibodies. Thus, the undesired side effects associated therewith are eliminated. A single treatment with such a serum leads to the suppression of primary and secondary antibody response. (compare for example, FIG. 2), as well as to the suppression of proliferative cellular immuno response It has been found that a single dose of the immuno-suppressive material of the present invention, together with antigen, leads also to the suppression of the secondary antibody response Furthermore, it has been shown that even repeated administration of antigen does not remove the suppressive effect. This is a substantial advantage in relation to the immuno-suppression agents generally utilized at the present time which require repeated administration for the maintenance of suppression.

Figure 3:
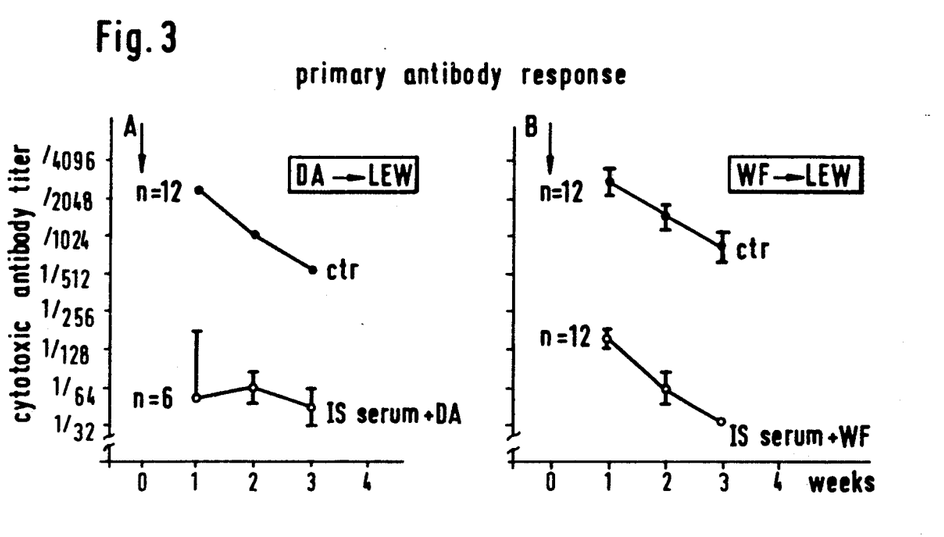

Experiments have further shown that the primary antibody response (see FIG. 3), as well as the secondary antibody response (see FIG. 4), are suppressed even against a third party donor through a single administration of the immuno-suppressive material of the present invention. Thus, an immuno-suppressive material of the present invention that has been obtained by BN cells coated with antibodies, suppresses not only the primary but also the secondary antibody response against unrelated third party donors, for example, DA and WF.

It was found that the suppression is dose dependent. According to the amount of IS-serum administered, there may be obtained a weak or total suppression of the antibody response. When lymphocytes are incubated in vitro with IS-serum, the Graft versus Host assay, shows a suppression of the proliferative T cell response.

Experiments have shown that the IS-serum produced in accordance with the present invention, contains a broadly reactive immuno-suppressive factor. The immuno-suppressive activity can be shown to be present in the IgG fraction. For example, thus it was found that 0 8 mg. of IS-IgG separated from the IS-serum by means of ion exchange chromatography, gave rise to a significant suppression of the antibody response in comparison to the untreated control or to a control treated with "normal" IgG (see FIG. 5). The effect can be shown, either in donor specific (BN-LEW) as well as non-specific (DA-LEW) systems.

Figure 5:
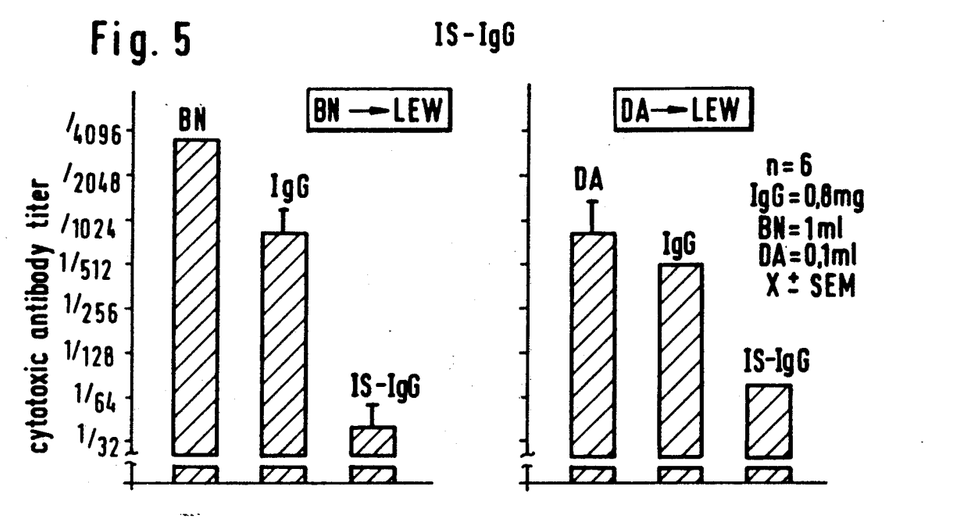

The experimental result shown in FIG. 5, was obtained in that 0.8 mg. of IS-IgG, together with BN or DA blood, were injected into LEW rats, while in the control animals, only blood or blood in connection with 0 8 mg. IgG from the serum of untreated rats, was utilized Further studies gave the result that the immuno-suppressive factor is an antibody which is directed against Neo-determinants of IgG, which are formed through antigen binding action (anti-Neo-IgG antibodies).

The immuno-suppressives formed in accordance with the present invention can be used for the suppression of humoral and/or cellular immune response and thus, can be successfully used in immuno-suppressive therapy as has been demonstrated hereinabove.

BRIEF DESCRIPTION OF THE DRAWINGS

FIGS. 3A and B are a plot of cytotoxic antibody titre against time for the primary antibody response caused by DA and WF blood respectively, with and without IS-serum.

FIGS. 4A and B are analogous to FIGS. 3A and B but showing the secondary antibody response.

FIGS. 5A and B are block graphs of cytotoxic antibody response upon administration of BN and DA blood respectively in the presence of "normal" IgG and IS-IgG.

WAYS OF CARRYING OUT THE INVENTION

The following examples serve to serve the further explanation of the invention under consideration.

GENERAL PROCEDURES

The following procedures exemplify generally accepted methods of isolation and purification.

Procedure 1

A. Immunization of Rabbits

New Zealand white rabbits (ca. 2 to 3 kgs.) are utilized. Approximately 1 ml. of blood is drawn from the rabbits and incubated with 1 mg. of human anti-rabbit erythrocyte IgG for 30–60 minutes at room temperature, the antibody excess is removed by washing 3 times with phosphate buffer. 1 ml. of this preparation is injected 3 times i.v., into the rabbit at 3 day intervals.

B. Mouse IS-Serum (i) BALB/c mice were utilized. 0.05 to 0.1 ml. of blood was removed from the mouse, incubated with 0.1 mg. human anti-mouse erythrocyte IgG for 30–60 minutes at room temperature, the excess antibodies removed by washing 3 times with phosphate buffer 0.1 ml. of this product was injected 3 to 5 times i.v , in weekly intervals into the mouse.

(ii) In an alternative procedure, anti-mouse IgG antibodies are extracted from the sera of human patients treated with monoclonal mouse IgG antibodies. IgG is prepared in the usual manner from this sera and 0.1 mg. of mouse IgG is then incubated with 0.1 mg. of human anti-mouse IgG for 60 minutes at room temperature and then as described above, repeatedly injected into the BALB/c mice. Three days after the last immunization, the spleen cells are removed from the mice and used for the preparation of monoclonal anti-human IgG antibodies by the well known procedure of Kohler and Milstein, Nature (1975) 256; 495.

Procedure 2

Preparation of IS-Serum

Blood is taken from the animals inoculated in accordance with the methods of Procedure #1 above and set aside at room temperature for from about 3 to about 24 hours. The blood is thus permitted to coagulate and then is centrifuged for 10 minutes at 4,000 rpm. An initial charge of 1 ml. of blood yields approximately 0.3 ml. of supernatant serum.

Procedure 3

A. IgG Separation by Ion Exchange Chromatography

There are utilized:
1. Mono-Q (5×50 mm. column) (Mono-Q is a product of Pharmacia).
2. Phosphate Buffer A (0.025 M pH 6.7)
3. Phosphate Buffer B (0.3 M pH 6.5)

0.2 ml. of the IS-serum is diluted with 0.8 ml. of phosphate buffer A and placed on the top of the column Elution is carried out at a flow rate of 2 ml./minute utilizing a gradient of 0/50%/100% phosphate buffer B for a total separation time of 15 minutes 1 ml. fractions were collected to yield 3 peaks. The first peak contains the IgG fraction.

The aforesaid IgG fraction is rebuffered over on a PD10 (Sephadex G25, Pharmacia) column which had previously been equilibrated with 20 ml. of phosphat buffer, pH 7.4. 2.5 ml. of IgG solution are placed on the column and eluted with phosphate buffer. There are thus provided approximately 3 ml. of rebuffered IgG solution which are further purified in accordance with procedure #4.

Procedure 4

Purification of IgG on a Protein A Column

There is utilized the Affi-Gel Protein A MAPS II (manufactured by Biorad) column , utilizing the binding buffer and elution buffer provided in the kit. The column volume is 2 ml. 3 ml. of the IgG solution obtained in accordance with with Procedure 3 are mixed with 3 ml. of the binding buffer and placed on the column. 30 ml. of binding buffer are washed through the column, followed by 10 ml. of the elution buffer. The 10 ml. of eluate are rebuffered on a PD10 column in pH 7 phosphate buffer in accordance with the procedure set forth in Procedure #3. The product, (i.e., 10 ml. IgG solution) is treated with 2 g. of Sephadex 25 to yield a concentrated IgG solution of about 1 ml. This product may be utilized as the IgG solution in the following examples or, if desired, it may be further purified by affinity chromatography in accordance with Procedure 5.

Procedure 5

Separation of Antibody by Affinity Chromatography

There is utilized a Sepharose column of 0.5 ml. containing Sepharose coated with human IgG at a concentration of 0.5 mg. IgG/ml. of Sepharose. 0.5 ml. of IS-IgG solution (IgG concentration 0.5 mg./ml.) are placed on the column. Thereafter, 2.5 ml. of elution buffer (as utilized in Procedure 4) are utilized for elution. The resulting IS antibodies (2.5 ml.) are rebuffered on the PD10 column (in accordance with the procedure of Procedure #3), there is thus obtained purified IS antibody of volume 3 ml. which may be utilized in this form.

EXAMPLE I

A. Rat IS-serum was produced, as schematically illustrated in FIG. 1, in the highly incompatible BN-LEW system, in the following manner:

1 ml. of BN blood was incubated at 20° C. for 30 minutes with 0.2 ml. of LEW-anti-BN serum. After the incubation, the excess antiserum was washed out and the cells resuspended to the original volume with phosphate buffer solution 1 ml. of cell suspension was injected 3 times i.v., into LEW rats in weekly intervals. The serum of the treated animals (IS) was collected one week later Only sera without cytotoxic anti-BN activity were used. In the experiments, IS serum and allogenic blood or leukocytes were injected i.v. into the recipients. The cytotoxic antibody titer was determined in weekly intervals.

A sample of IS-serum produced as described above, demonstrates a strong suppressive action without however containing cytotoxic antibodies. This removes the undesired side effects associated therewith A one-time treatment with such a serum in the rat, leads to suppression of the primary and secondary antibody response (see FIG. 2) with respect to blood cells with which the IS-serum was produced Furthermore, it has been shown that repeated antigen administration does not remove the suppression once it has been induced. This again, shows a substantial advantage with respect to presently generally utilized immuno-suppressives which require continual administration, in order to maintain the suppression.

B. The following experiments show that not only the primary antibody response, but also the secondary antibody response against a third party donor is suppressed by a single administration of IS-serum.

1 ml. of DA- or WF- blood was injected into LEW rats, together with 1 ml. of the IS-serum produced as above. Control animals received soley DA or WF blood. Examination showed suppression of the primary antibody response in the rats treated with IS-serum. The results of these experiments are set forth in FIG. 3.

Figure 4:
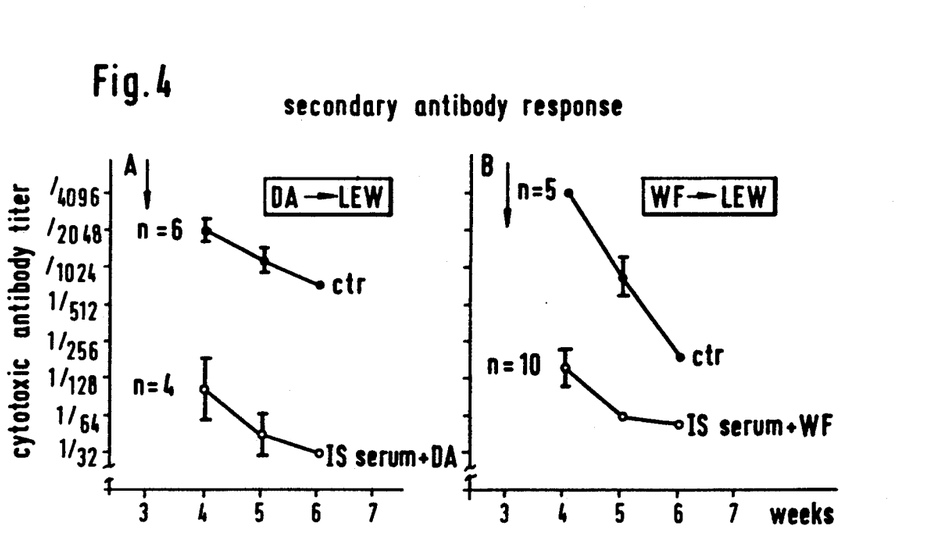

As shown in FIG. 4, 3 weeks after treatment with IS-serum, the animals were boosted with 1 ml. of DA or WF blood (without IS-serum). A significant suppression of antibody response to the DA or WF cells was found.

EXAMPLE II

Suppression of the Antibody with Thromobocyt Transfusion

Thrombocyte transfusion is a form of support therapy frequently utilized in human medicine. Patients who do not have hematological neoplasty can be given high dosage chemotherapy by means of thrombocyte substitution, whereas thrombocytopenic patients with primary bone marrow diseases, (i.e., acute leukemia), the thrombocyte transfusion by giving rise to a longer survival time, permits an effective therapy. The main problem of thrombocyte substitution is that generally speaking, sensitization of the patient against donor antigens will occur, which reduces the effectiveness of the transfusion. An experiment in this direction was carried out with LEW rats, which gave rise to the results which are set forth in FIG. 6.

Figure 6:
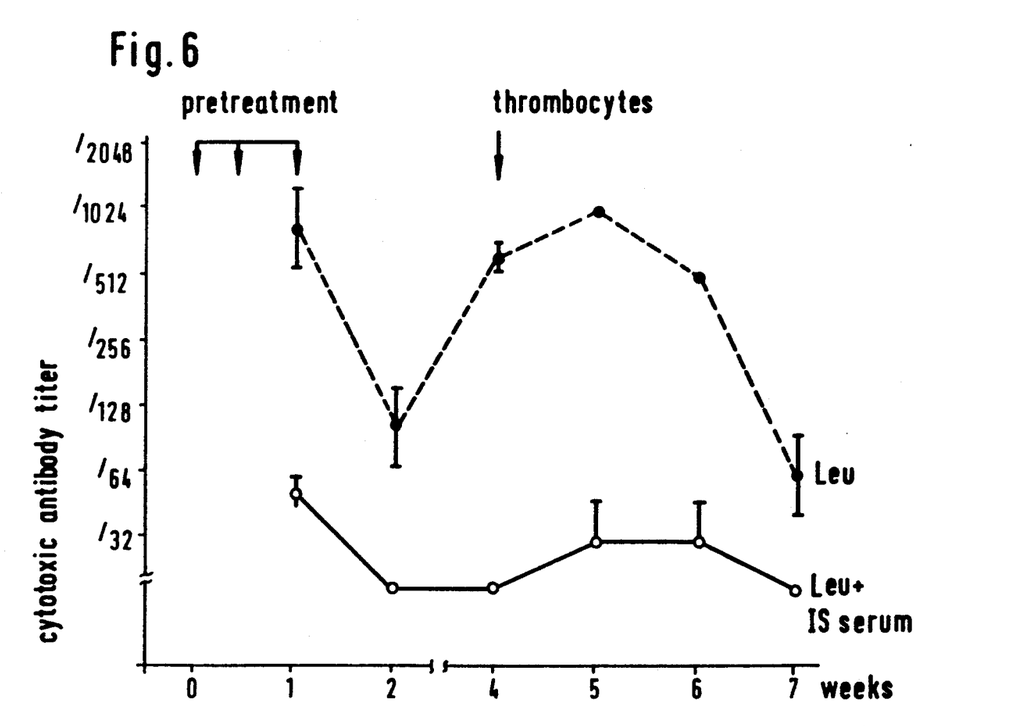
FIG. 6 is a plot of cytotoxic antibody titre against time for the administration of BN thrombocytes with and without IS-serum to LEW rats.

To LEW rats, there was given a 3 times administration (on days 0, 3 and 7), of $5 \times 10^6$ BN leucocytes (control animals) or $5 \times 10^6$ BN leucocytes, together with 0.2 ml. of the IS-serum obtained in the accordance with Example I. Three weeks later, both groups were boosted with $10^9$ BN thrombocytes (without IS-serum). In these experiments, the control LEW rats generated a strong anti-BN antibody response whereas with a simultaneous provision of IS-serum with the leucocytes to the LEW rats, the anti-thrombocyte antibody response was almost entirely suppressed.

EXAMPLE III

Suppression of Humoral Sensitization after Blood or Leucocyte Transfusion

In clinical kidney transplants, it has been found that the preparation of the potential recipient by means of blood transfusions, leads to a substantial improvement of survival of the transplant. However, pretransplant blood transfusion can lead to the formation of cytotoxic antibodies. If these antibodies are directed against the potential donor, the transplant cannot be carried out because of the risk of a hyperacute rejection. A portion of potential receptors, the so-called highly immunized patients, have a high percentage of cytotoxic antibodies so that it is exceedingly difficult to find a suitable donor. Even where a transplant for these patients is possible, the survival time of the transplant is shorter.

In living related kidney transplants, donor specific blood transfusions are often carried out. Approximately a third of the recipients develop anti-donor antibodies and so cannot be transplanted with the kidney of the prospective living donor. By avoiding the sensitization effect of the pretransplant blood transfusion, the positive influence of the blood transfusion upon the transplant survival can be considerably improved. It was found that the simultaneous treatment with blood transfusion and IS-serum, leads to a suppression of the cytotoxic and antibody response. This suppression remains even in further transplants.

Figure 2:
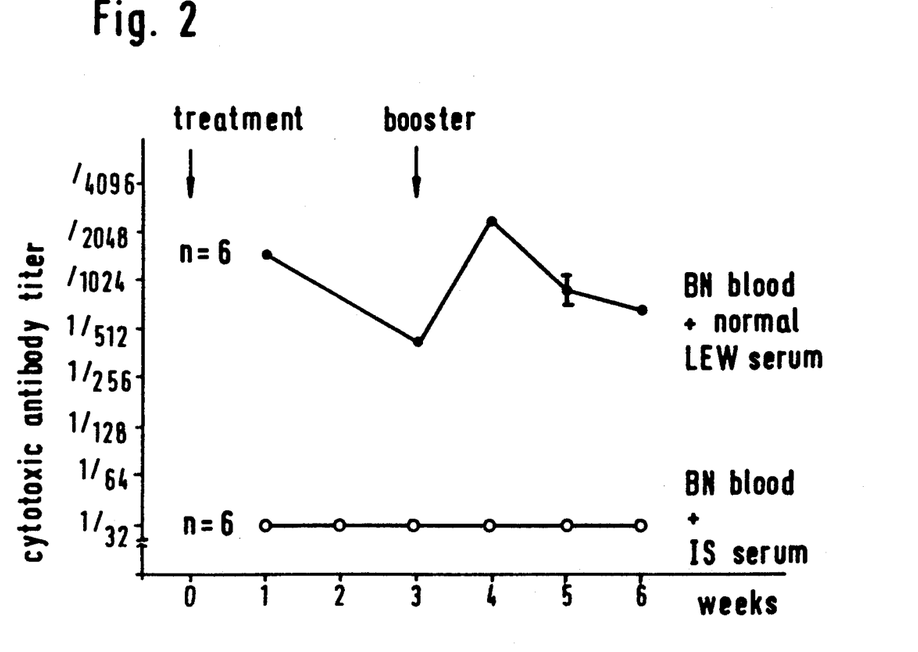
FIG. 2 is a plot of cytotoxic antibody titre against time for BN-blood+LEW serum and BN-blood+IS-serum.

Experiments results in this direction are set forth in FIG. 2. The results were obtained in the following manner.

LEW rats are injected on day 0 with 1 ml of the IS-serum obtained in accordance with Example I, together with 1 ml. of BN blood The control animals received only BN blood and normal LEW serum. As shown in FIG. 2, the groups of rats which received the IS-serum showed total suppression of the cytotoxic antibody response Three weeks later, both groups, that is to say, the control group and the group to which IS-serum was administered, were boosted with 1 ml of BN blood without IS-serum. The induced suppression remained even after the booster transfusion.

Figure 7:
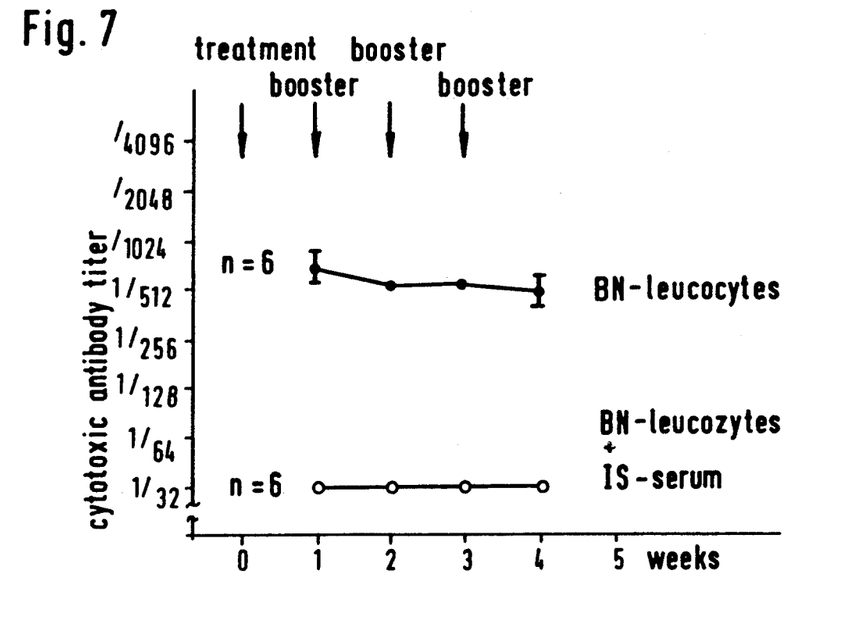
FIG. 7 is a plot of cytotoxic antibody titre against time for the administration of BN leucocytes with and without IS-serum to LEW rats, showing the effect of BN leucocyte booster in a LEW system with an without a single treatment with IS-serum.

Experiments in the rat have shown that the administration of a high dose of allogenous erythrocytes can lead to suppression of the antibody response. In order to eliminate a possible erythrocyte mediated suppression in blood transfusion experiments, LEW rats were transfused with BN leucocytes with or without administration of IS-serum (leucocytes are known to be strongly immunogenic and can lead to acceleration of rejection). Thus, on day 0, the LEW rats were injected with $5 \times 10$ BN leucocytes and 0.5 ml. of the IS-serum produced in accordance with Example I. The thus obtained results are shown in FIG. 7. As can be seen from FIG. 7, a single administration of IS-serum gave rise to a total suppression of antileucocyte antibody response which persisted even after repeated booster transfusions (without IS-serum) with cells of the same donor

EXAMPLE IV

Suppression of the Graft verus Host (GvH Reaction)

The GvH reaction has a considerable influence upon the success of clinical bone marrow transplants. In spite of many attempts, there is no clear solution for this problem The experiments with rats have shown that the pretreatment of the lymphocyte donor or the incubation of lymphocytes with IS-serum, lead to a considerable reduction of the GVH reaction. The experiments were carried out in the following manner.

Figure 8:
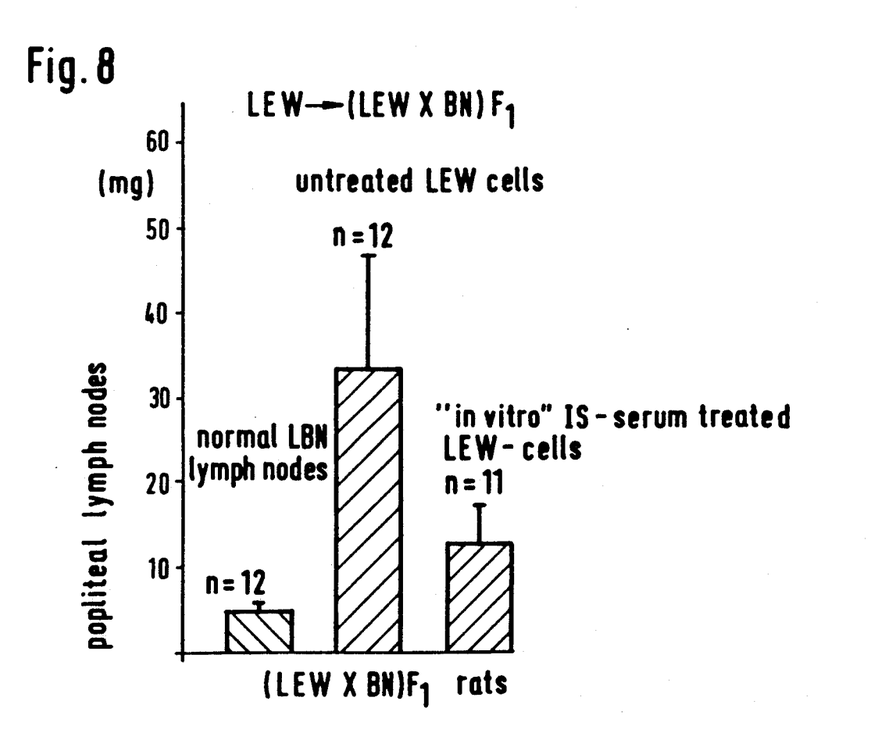
FIG. 8 is a bar graph of lymph node weight showing normal lymph nodes of LBN rats, nodes after injection of untreated LEW cells and LEW cells treated with IS-serum.

$5 \times 10$ LEW spleen cells were twice incubated at 22° C. for 90 minutes with 0.5 ml. of the IS-serum produced in accordance with Example I. After each incubation, the cells were washed. LBN-rats (that is to say, LEW $\times$ BN) were injected with $5 \times 10$ with treated or untreated spleen cells subcutaneously into the footpads. Five days later, the popliteal lymph nodes were removed and weighed. The results obtained are set forth in FIG. 8. As will shown, there is demonstrated, a very strong suppression of the GvH reaction.

EXAMPLE V

Possible Prolongation of Kidney Transplant Survival Through Treatment with Antibody Coated Cells Where LEW rats are treated prior to transplantation with antibody coated BN cells without further immunosuppressive therapy, a substantial increase in the survival time of BN kidneys is noted. This was confirmed by the following experiments.

Figure 9:
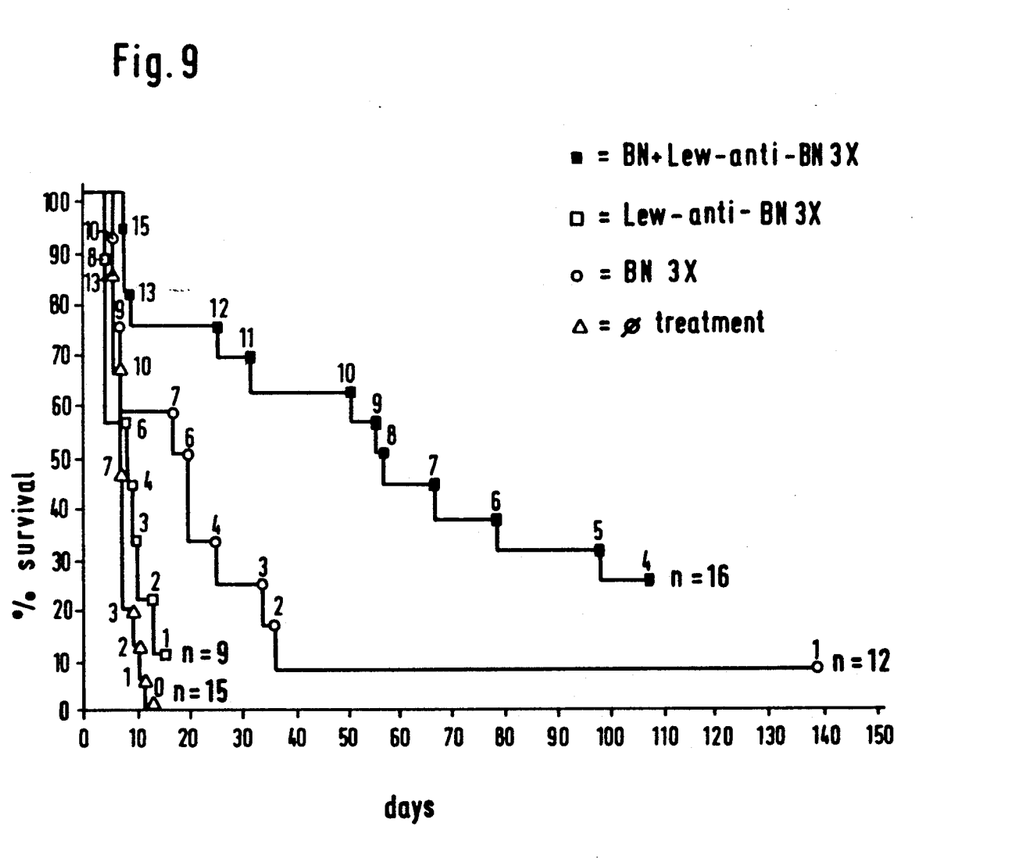
FIG. 9 is a plot of % survival against time of LEW rats receiving kidney transplants which prior to transplant, had been treated with BN cells previously incubated with LEW anti-BN serum, with LEW anti-BN serum only, with untreated BN blood and with no pretreatment at all.

LEW rats were treated 3 times, in weekly intervals, with cells, which were obtained from 1 ml of BN blood which had been incubated with 0.05 ml. LEW anti-BN serum and subsequently washed 3 times with phosphate buffer solution. The control animals were pretreated with 0.05 ml. LEW-anti-BN-serum or untreated BN blood, or not pretreated at all. The results of these experiments are shown in FIG. 9. The survival time ($X \pm$ standard error) of the animals which had been pretreated with antibody coated cells, were shown to be in the region of $109 \pm 27$ days, in contrast to the control animals with had a survival time of $8.4 \pm .4$ days.

EXAMPLE VI

Rabbit IS-serum was obtained by the immunization of rabbits with autologous or allogeneic blood cells covered by human antibodies. These experiments were based on the knowledge that humans can spontaneously generate antibodies against rabbit erythrocytes. Thus, there exists the possibility of coating rabbit cells with human IgG. One ml. of rabbit blood was incubated for 30 minutes with 1.5 mg. of human IgG antibodies. The excess of antibodies was washed out and the rabbits were immunized 3 times in 3 day intervals with the antibody covered cells by intravenous administration. One week later, the IS-serum was collected Neither in autologous nor in allogenic IS-serum, could human anti-lymphocyte antibodies be found.

Rabbit IS-serum was tested in vitro for suppression of the activity of human B and T cells. The results showed that all sera suppressed the B cell response by 50 to 82% (measured by the indirect plaque forming cell assay with pokeweed mitogen stimulation). The allogenic IS-serum was more strongly suppressive than the autologous IS-serum. A suppression of the proliferative (MLC) and cytotoxic (CML) T cell response could similarly be demonstrated. Again, a stronger effect of the allogenic IS-serum was detected.

We claim:

1. A process for the production of an immuno-suppressive serum containing IS-IGG comprising the steps of:
   (a) incubating animal cells with homologous or heterologous antibodies, which specifically bind to said cells, whereby said cells are coated with said antibodies,
   (b) washing said incubated cells,
   (c) multiply injecting said cells into a recipient animal,
   (d) after a predetermined incubating time, taking the blood from the recipient animal and separating the serum therefrom.

2. A process of claim 1 comprising the additional step of separating the IgG from said serum.

3. A process according to claim 1, wherein the cells are blood cells.

4. A process in accordance with claim 1, wherein the anitbody coated cells are reinjected into a recipient animal which is the same as the donor animal originally donating the uncoated cells.

5. A process in accordance with claim 1, wherein the antibody coated cells are injected into a recipient animal other than the donor of the uncoated cells.

6. A process according to claim 5, wherein the recipient animal is an animal of the same or different species from the donor animal.

* * * * *